(12) United States Patent
Johnson

(10) Patent No.: US 7,540,899 B1
(45) Date of Patent: Jun. 2, 2009

(54) SHAPE MEMORY ALLOY THIN FILM, METHOD OF FABRICATION, AND ARTICLES OF MANUFACTURE

(75) Inventor: A David Johnson, San Leandro, CA (US)

(73) Assignee: TiNi Alloy Company, San Leandro, CA (US)

( * ) Notice: Subject to any disclaimer, the term of this patent is extended or adjusted under 35 U.S.C. 154(b) by 395 days.

(21) Appl. No.: 11/420,157

(22) Filed: May 24, 2006

Related U.S. Application Data

(60) Provisional application No. 60/683,891, filed on May 25, 2005.

(51) Int. Cl.
C22B 9/16 (2006.01)
C22B 9/22 (2006.01)

(52) U.S. Cl. .................. 75/10.11; 148/561; 148/562; 148/563

(58) Field of Classification Search .................. None
See application file for complete search history.

(56) References Cited

U.S. PATENT DOCUMENTS

| | | | |
|---|---|---|---|
| 1,560,335 A | 11/1925 | Czochralski |
| 1,926,925 A | 9/1933 | Wescott |
| 2,060,593 A | 11/1936 | Schaurte et al. |
| 2,371,614 A | 3/1945 | Graves |
| 2,586,556 A | 2/1952 | Mullikin |
| 2,608,996 A | 9/1952 | Forman |
| 2,610,300 A | 9/1952 | Walton et al. |
| 2,647,017 A | 7/1953 | Coullette |
| 2,911,504 A | 11/1959 | Cohn |
| 3,229,956 A | 1/1966 | White |
| 3,351,463 A | 11/1967 | Rozner et al. |
| 3,357,432 A | 12/1967 | Sparks |
| 3,400,906 A | 9/1968 | Stocklin |

(Continued)

FOREIGN PATENT DOCUMENTS

EP 0053596 6/1982

(Continued)

OTHER PUBLICATIONS

Johnson, David et al.; U.S. Appl. No. 12/019,553 entitled "Frangible shape memory alloy fire sprinkler valve actuator," filed Jan. 24, 2008.

(Continued)

*Primary Examiner*—George Wyszomierski
(74) *Attorney, Agent, or Firm*—Shay Glenn LLP

(57) ABSTRACT

A method of forming a single crystal in a thin film by progressively rapidly heating (and cooling) a narrow band of amorphous material. The amorphous thin film may be of shape memory alloy such as TiNi or CuAlNi. Heating may be accomplished by a line-focused laser beam. The thin film may be formed by sputter deposition on a substrate such as silicon. The thin film crystal that is formed has non-isotropic stress/strain characteristics, and very large recoverable strain in a preferred direction. The single crystal SMA exhibits greater strain recovery; Constant force deflection; Wider transition temperature range; Very narrow loading hysteresis; and Recovery that is repeatable & complete. Single Crystal SMA is manufactured by pulling a single crystal from melt, a method similar to that used by the semiconductor industry to fabricate silicon boules. This process enables manufacture of materials that approach theoretical limits.

13 Claims, 4 Drawing Sheets

U.S. PATENT DOCUMENTS

| | | | |
|---|---|---|---|
| 3,408,890 A | 11/1968 | Bochman, Jr. | |
| 3,445,086 A | 5/1969 | Quinn | |
| 3,454,286 A | 7/1969 | Anderson et al. | |
| 3,546,996 A | 12/1970 | Grijalva et al. | |
| 3,613,732 A | 10/1971 | Willson et al. | |
| 3,620,212 A | 11/1971 | Fannon, Jr. et al. | |
| 3,659,625 A | 5/1972 | Coiner et al. | |
| 3,725,835 A | 4/1973 | Hopkins et al. | |
| 3,849,756 A | 11/1974 | Hickling | |
| 3,918,443 A | 11/1975 | Vennard et al. | |
| 3,974,844 A | 8/1976 | Pimentel | |
| 4,055,955 A | 11/1977 | Johnson | |
| 4,063,831 A | 12/1977 | Meuret | |
| 4,072,159 A | 2/1978 | Kurosawa | |
| 4,096,993 A | 6/1978 | Behr | |
| 4,176,719 A | 12/1979 | Bray | |
| 4,177,327 A | 12/1979 | Mathews | |
| 4,195,773 A | 4/1980 | Ogden | |
| 4,243,963 A | 1/1981 | Jameel et al. | |
| 4,265,684 A * | 5/1981 | Boll | 148/121 |
| 4,279,790 A | 7/1981 | Nakajima | |
| 4,340,049 A | 7/1982 | Munsch | |
| 4,485,545 A | 12/1984 | Caverly | |
| 4,501,058 A | 2/1985 | Schutzler | |
| 4,524,343 A | 6/1985 | Morgan et al. | |
| 4,549,717 A | 10/1985 | Dewaegheneire | |
| 4,551,974 A | 11/1985 | Yaeger et al. | |
| 4,553,393 A | 11/1985 | Ruoff | |
| 4,558,715 A | 12/1985 | Walton et al. | |
| 4,567,549 A | 1/1986 | Lemme | |
| 4,585,209 A | 4/1986 | Aine et al. | |
| 4,589,179 A | 5/1986 | Hulting, Jr. | |
| 4,596,483 A | 6/1986 | Gabriel et al. | |
| 4,619,284 A | 10/1986 | Delarue et al. | |
| 4,654,191 A | 3/1987 | Krieg | |
| 4,684,913 A | 8/1987 | Yaeger | |
| 4,706,758 A | 11/1987 | Johnson | |
| 4,753,465 A | 6/1988 | Dalby | |
| 4,821,997 A | 4/1989 | Zdeblick | |
| 4,823,607 A | 4/1989 | Howe et al. | |
| 4,824,073 A | 4/1989 | Zdeblick | |
| 4,848,388 A | 7/1989 | Waldbusser | |
| 4,854,797 A | 8/1989 | Gourd | |
| 4,864,824 A | 9/1989 | Gabriel et al. | |
| 4,893,655 A | 1/1990 | Anderson | |
| 4,896,728 A | 1/1990 | Wolff et al. | |
| 4,943,032 A | 7/1990 | Zdeblick | |
| 5,060,888 A | 10/1991 | Vezain et al. | |
| 5,061,137 A | 10/1991 | Gourd | |
| 5,061,914 A | 10/1991 | Busch et al. | |
| 5,069,419 A | 12/1991 | Jerman | |
| 5,072,288 A | 12/1991 | MacDonald et al. | |
| 5,114,504 A | 5/1992 | AbuJudom, II et al. | |
| 5,116,252 A | 5/1992 | Hartman | |
| 5,117,916 A | 6/1992 | Ohta et al. | |
| 5,119,555 A | 6/1992 | Johnson | |
| 5,129,753 A | 7/1992 | Wesley et al. | |
| 5,160,233 A | 11/1992 | McKinnis | |
| 5,190,546 A | 3/1993 | Jervis | |
| 5,192,147 A | 3/1993 | McCloskey | |
| 5,211,371 A | 5/1993 | Coffee | |
| 5,218,998 A | 6/1993 | Bakken et al. | |
| 5,245,738 A | 9/1993 | Johnson | |
| 5,309,717 A | 5/1994 | Minch | |
| 5,312,152 A | 5/1994 | Woebkenberg, Jr. et al. | |
| 5,325,880 A | 7/1994 | Johnson et al. | |
| 5,344,117 A | 9/1994 | Trah et al. | |
| 5,364,046 A | 11/1994 | Dobbs et al. | |
| 5,494,113 A | 2/1996 | Polan | |
| 5,502,982 A | 4/1996 | Venetucci | |
| 5,543,349 A | 8/1996 | Kurtz et al. | |
| 5,605,543 A | 2/1997 | Swanson | |
| 5,619,177 A | 4/1997 | Johnson et al. | |
| 5,622,225 A | 4/1997 | Sundholm | |
| 5,640,217 A | 6/1997 | Hautcoeur et al. | |
| 5,641,364 A | 6/1997 | Golberg et al. | |
| 5,676,356 A | 10/1997 | Ekonen et al. | |
| 5,695,504 A | 12/1997 | Gifford, III et al. | |
| 5,714,690 A | 2/1998 | Burns et al. | |
| 5,722,989 A | 3/1998 | Fitch et al. | |
| 5,771,742 A | 6/1998 | Bokaie et al. | |
| 5,772,378 A | 6/1998 | Keto-Tokoi | |
| 5,796,152 A | 8/1998 | Carr et al. | |
| 5,819,749 A | 10/1998 | Lee et al. | |
| 5,825,275 A | 10/1998 | Wuttig et al. | |
| 5,837,394 A | 11/1998 | Schumm, Jr. | |
| 5,840,199 A | 11/1998 | Warren | |
| 5,850,837 A | 12/1998 | Shiroyama et al. | |
| 5,867,302 A | 2/1999 | Fleming | |
| 5,903,099 A | 5/1999 | Johnson et al. | |
| 5,924,492 A | 7/1999 | Kikuchi et al. | |
| 5,930,651 A | 7/1999 | Terasawa | |
| 5,960,812 A | 10/1999 | Johnson | |
| 6,042,553 A | 3/2000 | Solar et al. | |
| 6,072,617 A | 6/2000 | Henck | |
| 6,073,700 A | 6/2000 | Tsuji et al. | |
| 6,075,239 A | 6/2000 | Aksyuk et al. | |
| 6,084,849 A | 7/2000 | Durig et al. | |
| 6,101,164 A | 8/2000 | Kado et al. | |
| 6,124,523 A | 9/2000 | Banas et al. | |
| 6,126,371 A | 10/2000 | McCloskey | |
| 6,139,143 A | 10/2000 | Brune et al. | |
| 6,195,478 B1 | 2/2001 | Fouquet | |
| 6,203,715 B1 | 3/2001 | Kim et al. | |
| 6,229,640 B1 | 5/2001 | Zhang | |
| 6,247,493 B1 | 6/2001 | Henderson | |
| 6,277,133 B1 | 8/2001 | Kanesaka | |
| 6,284,067 B1 * | 9/2001 | Schwartz et al. | 148/525 |
| 6,386,507 B2 | 5/2002 | Dhuler et al. | |
| 6,406,605 B1 | 6/2002 | Moles | |
| 6,407,478 B1 | 6/2002 | Wood et al. | |
| 6,410,360 B1 | 6/2002 | Steenberge | |
| 6,447,478 B1 | 9/2002 | Maynard | |
| 6,451,668 B1 | 9/2002 | Neumeier et al. | |
| 6,454,913 B1 | 9/2002 | Rasmussen et al. | |
| 6,470,108 B1 | 10/2002 | Johnson | |
| 6,475,261 B1 | 11/2002 | Matsumoto et al. | |
| 6,524,322 B1 | 2/2003 | Berreklouw | |
| 6,533,905 B2 | 3/2003 | Johnson et al. | |
| 6,537,310 B1 | 3/2003 | Palmaz et al. | |
| 6,582,985 B2 | 6/2003 | Cabuz et al. | |
| 6,592,724 B1 | 7/2003 | Rasmussen et al. | |
| 6,605,111 B2 | 8/2003 | Bose et al. | |
| 6,614,570 B2 | 9/2003 | Johnson et al. | |
| 6,620,634 B2 | 9/2003 | Johnson et al. | |
| 6,624,730 B2 | 9/2003 | Johnson et al. | |
| 6,669,794 B1 * | 12/2003 | Bellouard et al. | 148/563 |
| 6,669,795 B2 | 12/2003 | Johnson et al. | |
| 6,672,502 B1 | 1/2004 | Paul et al. | |
| 6,688,828 B1 | 2/2004 | Post | |
| 6,729,599 B2 | 5/2004 | Johnson | |
| 6,742,761 B2 | 6/2004 | Johnson et al. | |
| 6,746,890 B2 | 6/2004 | Gupta et al. | |
| 6,771,445 B1 | 8/2004 | Hamann et al. | |
| 6,790,298 B2 | 9/2004 | Johnson et al. | |
| 6,811,910 B2 | 11/2004 | Tsai et al. | |
| 6,840,329 B2 | 1/2005 | Kikuchi et al. | |
| 6,843,465 B1 | 1/2005 | Scott | |
| 6,908,275 B2 | 6/2005 | Nelson et al. | |
| 6,920,966 B2 | 7/2005 | Buchele et al. | |
| 6,955,187 B1 | 10/2005 | Johnson | |
| 7,040,323 B1 | 5/2006 | Menchaca et al. | |
| 7,044,596 B2 | 5/2006 | Park | |
| 7,084,726 B2 | 8/2006 | Gupta et al. | |

| | | | |
|---|---|---|---|
| 7,201,367 | B2 | 4/2007 | Wietharn |
| 2001/0023010 | A1 | 9/2001 | Yamada et al. |
| 2002/0018325 | A1 | 2/2002 | Nakatani et al. |
| 2002/0062154 | A1 | 5/2002 | Ayers |
| 2003/0002994 | A1 | 1/2003 | Johnson et al. |
| 2003/0078465 | A1 | 4/2003 | Pai et al. |
| 2003/0170130 | A1 | 9/2003 | Johnson |
| 2004/0200551 | A1 | 10/2004 | Brhel et al. |
| 2004/0243219 | A1 | 12/2004 | Fischer et al. |
| 2004/0249399 | A1 | 12/2004 | Cinquin et al. |
| 2005/0113933 | A1 | 5/2005 | Carter et al. |
| 2006/0118210 | A1 | 6/2006 | Johnson |
| 2006/0213522 | A1 | 9/2006 | Menchaca et al. |
| 2007/0137740 | A1 | 6/2007 | Johnson et al. |
| 2007/0246233 | A1 | 10/2007 | Johnson |

FOREIGN PATENT DOCUMENTS

| | | |
|---|---|---|
| EP | 0310439 | 4/1989 |
| EP | 1122526 | 8/2001 |
| EP | 1238600 | 9/2002 |
| GB | 2187951 | 9/1987 |
| JP | 57/161031 A * | 10/1982 |
| JP | 59179771 | 10/1984 |
| JP | 07090624 | 4/1995 |
| JP | 10173306 | 6/1998 |
| JP | 2000185999 A | 7/2000 |
| SU | 1434314 | 10/1988 |
| WO | WO98/53362 | 11/1998 |
| WO | WO00/04204 | 1/2000 |
| WO | WO03/052150 | 6/2003 |
| WO | WO2005/108635 | 11/2005 |

OTHER PUBLICATIONS

Antonov et al.; New advances and developments in the Stepnakov method for the growth of shaped crystals; Crystallography Reports; vol. 47; Suppl. 1; 2002; pp. S43-S52.

ElastametTM brochure from New Discovery Metals; 2007.

ElastametTM website screen capture, accessed Jul. 23, 2008.

Fu et al.; The growth characteristics with a shape memory effect; J. Phys.: Condens. Matter; vol. 4; 1992; pp. 8303-8310.

Morgan; Medical shape memory alloy applications—the market and its products; Materials Science and engineering A 378; 2004; pp. 16-23.

Qingfu et al.; Stabilisation of martensite during training of Cu-Al-Ni single crystals; Journal de Physique IV; Collloqu C2; Supplement to the Journa de Physique III; vol. 5; Feb. 1995; pp. 181-186.

Recarte et al.; Influence of Al and Ni concentration on the martensitic transformation in Cu-Al-Ni shape-memory alloys; Metallurgical and Materials Transactions A; vol. 33A; Aug. 2002; pp. 2581-2591.

Sittner et al.; Stress induced martensitic transformations in tension/torsion of CuAlNi single crystal tube; Scripta Materialia; vol. 48; 2003; pp. 1153-1159.

Sutuo et al.; Development of medical guide wire of Cu-Al-Mn-base superelastic alloy with functionally graded characteristics; Mater Res Part B: Appl Biomater; vol. 69B; 2004; pp. 64-69.

Zhang et al.; The variant selection criteria in single-crystal CuAlNi shape memory alloys; Smart Mater. Struct.; vol. 9; 2000; pp. 571-581.

Zhdanov et al.; Thermal stresses in tubes, produced from a melt by the Stepanov method, during their coiling; Journal of Engineering Physics and Thermophysics; vol. 68; No. 1; 1995; pp. 80-89.

Johnson, David et al.; U.S. Appl. No. 10/972,745 entitled "Non-explosive releasable coupling device," filed Oct. 25, 2004.

Xiaogdang, MA; U.S. Appl. No. 10/972,759 entitled "Magnetic data storage system," filed Oct. 25, 2004.

Johnson, David et al.; U.S. Appl. No. 11/006,501 entitled "Anastomosis device and method," filed Dec. 6, 2004.

Johnson, David et al.; U.S. Appl. No. 11/041,185 entitled "Single crystal Shape memory alloy devices and methods," filed Jan. 24, 2005.

Johnson, David; U.S. Appl. No. 11/396,234 entitled "Tear-resistant thin film methods of fabrication," filed Mar. 31, 2006.

Johnson, David; U.S. Appl. No. 11/415,885 entitled "Eyeglass frame," filed May 2, 2006.

Johnson, David; U.S. Appl. No. 11/526,138 entitled "Constant load bolt," filed Sep. 22, 2006.

Johnson, David; U.S. Appl. No. 11/859,697 entitled "Constant load fastener," filed Sep. 21, 2007.

I. E. Viahhi; Robototechnic Constructions Based On CU-AL-NI Single Crystal Actuators; Proceedings of Second International Conference on Shape Memory and Superelastic Technologies; 1997; United States.

Pauling, Linus, College Chemistry, second edition, W.H. Freeman and Company, San Francisco, 1955, pp. 81-91.

Buchaillot L. et al., "Thin film of titanium/nickel shape memory alloy for multi-degree of freedom microactuators", Seisan Kenkyu, vol. 51, No. 8, 1999, pp. 22-23.

Johnson A. D. et al., "Application of shape memory alloys: advantages, disadvantages, and limitations", Micromachining and Microfabrication Process Technology VII, Oct. 22-24, 2001, San Francisco, CA, USA, vol. 4557, 2001, pp. 341-351.

Takabayashi et al., "Reversible shape memory alloy film fabricated by RF sputtering", Materials and Manufacturing Processes, vol. 13, No. 2, 1998, pp. 275-286.

Martynov, V., "TiNi thin films for microactuators and microdevices: sputter deposition and processing techniques", Thermec' 2003, Internat'l Conf. on Processing and Manufacturing of Advanced Materials, Jul. 7-11, 2003, Leganes, Madrid, Spain, Materials Science Forum, Jul. 7, 2003 vol. 426-432; pp. 3475-3480.

Johnson, David et al.; U.S. Appl. No. 11/948,852 entitled "Method of alloying reactive elemental components," filed Nov. 30, 2007.

Johnson, David et al.; U.S. Appl. No. 11/949,663 entitled "Hyperelastic shape setting devices and fabrication methods," filed Dec. 3, 2007.

Johnson, Alfred David; U.S. Appl. No. 12/182,119 entitled "Method and devices for preventing restenosis in cardiovascular stents," filed Jul. 29, 2008.

* cited by examiner

SHAPE MEMORY ALLOY THIN FILM, METHOD OF FABRICATION, AND ARTICLES OF MANUFACTURE

CROSS-REFERENCE

This application claims the benefit of U.S. Provisional Application No. 60/683,891, filed May 25, 2005, which is incorporated herein by reference in its entirety.

FIELD OF THE INVENTION

The present invention relates to shape memory alloys (SMA), and more particularly to thin film superelastic single-crystal shape memory alloys (single crystal SMA or SCSMA) and multiple crystal SMA.

BACKGROUND OF THE INVENTION

Nitinol or NiTi or TiNi is an alloy of titanium nickel that undergoes an energetic crystalline phase change at near-ambient temperatures: these different phases have distinctly different mechanical characteristics giving rise to a shape change and accompanied by superelasticity. The superelastic properties of SMA are discussed in Shape Memory Materials, K Otsuka et al. eds. (Cambridge University Press 1998), pp. 27 et seq.

TiNi (generic name is Nitinol) shape memory alloy is commonly used in aerospace, medicine, and consumer products. Thin film SMA has been made in laboratory quantities since 1989. Both bulk and thin film forms are polycrystalline. Single crystal SMA, having a martensitic phase transformation, has much greater superelasticity than polycrystalline SMA. Some SMAs such as Cu—Al—Ni can be made in single crystal form as they are pulled from melt and quenched. These crystals are not limited in length except for the capacity of the machine. TiNi is difficult to grow in this way, and single crystals are generally only a fraction of a centimeter long.

Thin film TiNi is formed by vacuum sputter deposition. A process of crystallization consists of heating to near 500 degrees C., at which temperature many small crystals originate and coalesce into a crystalline form which has the shape memory property.

Single crystals of bulk material are formed by pulling molten material by surface tension to produce a moving crystallization front that progresses through the crystal as it is pulled. The Czochralski method for Silicon and Stepanov method for alloys are examples. These processes work by transforming the molten material (alloy or silicon) from a completely un-structured atomic arrangement to one that is completely ordered as it solidifies. Since in the initial state there are no grain boundaries to interfere with growth of the crystal, it grows as a single crystal in a preferred direction (with a crystallographic index value of <100> for Cu—Al—Ni).

Thin films of alloys, particularly TiNi, are formed as an amorphous layer which has no atomic order. Heating to an elevated temperature (490-520 degree C. for TiNi) allows crystals to form and to grow. When heating is uniform, especially if heating (and cooling) is slow, many nano-crystals form and grow simultaneously. However, by analogy with crystals pulled from melt, if a narrow crystallization front is moved through the thin film expanse by a process that rapidly heats and cools the material, it may be expected to crystallize along a preferred direction and form a single crystal in the same manner as a material pulled from melt.

Another method of forming a single crystal thin film is by use of a substrate with appropriate lattice parameters to grow a crystal epitaxially. The vertical structure will permit larger deformations in the vertical direction and may be appropriate for nano memory applications.

Other methods and processes may be employed to enhance the ability of thin film to grow as a single crystal. In particular, a 'Fiber' texture may be induced in the substrate, and ion beam assisted deposition has been successfully used with other thin films to achieve epitaxial growth.

Nitinol materials are used in numerous applications. Superelastic eyeglass frames and components have been known for years, and they are a major selling item in eyeglass manufacturing and retail. Such materials are polycrystalline, and hence the maximum recoverable strain is not achieved because not all crystal domains are oriented in a favorable direction. Superelastic Nitinol is also used in intravascular medical intervention.

SUMMARY OF THE INVENTION

An aspect of this invention provides for creating a thin film of amorphous material that is a single crystal rather than polycrystalline form, by controlling the microstructure formation during crystal growth. From this process, oriented crystals with no grain boundaries evolve. The single crystal can be described as textured because the thinness of the film results in an apparent loss of some of the crystal variants. Further, a method is provided for fabricating a single crystal thin film comprising the steps of rapidly heating a shape memory alloy material to crystallization temperature with a simultaneous scanning motion so that a crystallization front or line moves or sweeps across the span of the film. Ahead of the front the material is amorphous. In the region of the front the material is hot enough to propagate a single crystal or a plurality of parallel crystals. Behind the crystallization front the material is a single crystal with a single crystal orientation.

The invention further comprises articles of manufacture of single crystal thin films, especially shape memory alloy thin films. Such single crystal thin film has on the order of more than twice the recoverable strain of polycrystalline form. The strain is directional.

Yet another aspect of the invention includes sputter depositing a thin film of amorphous metal onto a substrate, heating the thin film so that it reaches the crystallization temperature in a narrow line or band, moving the heated line or band across the surface at such a rate that the crystal forms rapidly under the heat, creating a moving crystallization front, and cooling behind the front so that the single crystal formed is stabilized.

In an aspect of the invention, a method for making shape memory alloy thin film is provided. The method comprises the steps of: depositing a layer of amorphous material on a substrate; applying heat to a strip of the amorphous material; moving the heat source across the amorphous material to heat sequential strips of material; crystallizing the amorphous material into crystallized material having a crystallographic orientation; and cooling the crystallized material with a heat sink. In some embodiments, the method can also include the step of using a seed crystal as a starting material. Suitable crystallized materials include materials that are superelastic at room temperature. Heat can be provided by any suitable source. Suitable sources include, for example, devices selected from the group comprising: laser, infrared wavelength light source, visible wavelength light source. Heat can also be provided by a scanning electron beam. Once the material is made a wide variety of devices can be manufactured from the material. Suitable devices include, but are not limited to microactuator, valve, electric switch, relay, optical switch, stent, stent covers, and anastomosis devices.

In another aspect of the invention, a method for forming a thin film of shape memory alloy comprising the steps of: sputter depositing a thin film of amorphous metal onto a substrate, heating a narrow band of the thin film so that it reaches the crystallization temperature, heating sequential narrow bands of the thin film to create a crystallization front, and cooling behind the crystallization front to stabilize the single crystal. As with previous embodiments, the method can also be adapted to include obtaining and/or using a seed crystal as a starting material. Additionally, once the material is made a wide variety of devices can be manufactured from the material.

A shape memory alloy comprising an alloy formed from the steps of: depositing a layer of amorphous material on a substrate; applying heat to a narrow strip of the amorphous material to its crystallization temperature; heating sequential narrow strips of amorphous material to a crystallization temperature; and cooling the crystallized material with a heat sink. As with previous embodiments, the method can also be adapted to include obtaining and/or using a seed crystal as a starting material. Additionally, once the material is made a wide variety of devices can be manufactured from the material.

A shape memory alloy comprising an alloy formed from the steps of: sputter depositing a thin film of amorphous metal onto a substrate, heating the thin film so that it reaches a crystallization temperature in a narrow line or band, moving the heated line or band across the surface at such a rate that the crystal forms rapidly under the heat, creating a moving crystallization front, and cooling behind the front to form a stabilized single crystal. As with previous embodiments, the method can also be adapted to include obtaining and/or using a seed crystal as a starting material or to initiate the crystallization process. Additionally, once the material is made a wide variety of devices can be manufactured from the material.

In yet another aspect, a method of manufacturing a device from a shape memory alloy thin film comprising the steps of: depositing a layer of amorphous material on a substrate; applying heat to a strip of the amorphous material; moving the heat source across the amorphous material to heat sequential strips of material; crystallizing the amorphous material into crystallized material; providing a heat sink so that the crystallized material is quickly cooled; manufacturing a device from the crystallized material. Suitable devices include, but are not limited to, microactuators, valves, electric switches, relays, optical switches, stents, stent covers, and anastomosis devices.

The shape memory alloys of the invention can be single crystal shape memory alloys or multiple crystal shape memory alloy.

INCORPORATION BY REFERENCE

All publications, patents and patent applications mentioned in this specification are herein incorporated by reference to the same extent as if each individual publication, patent or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
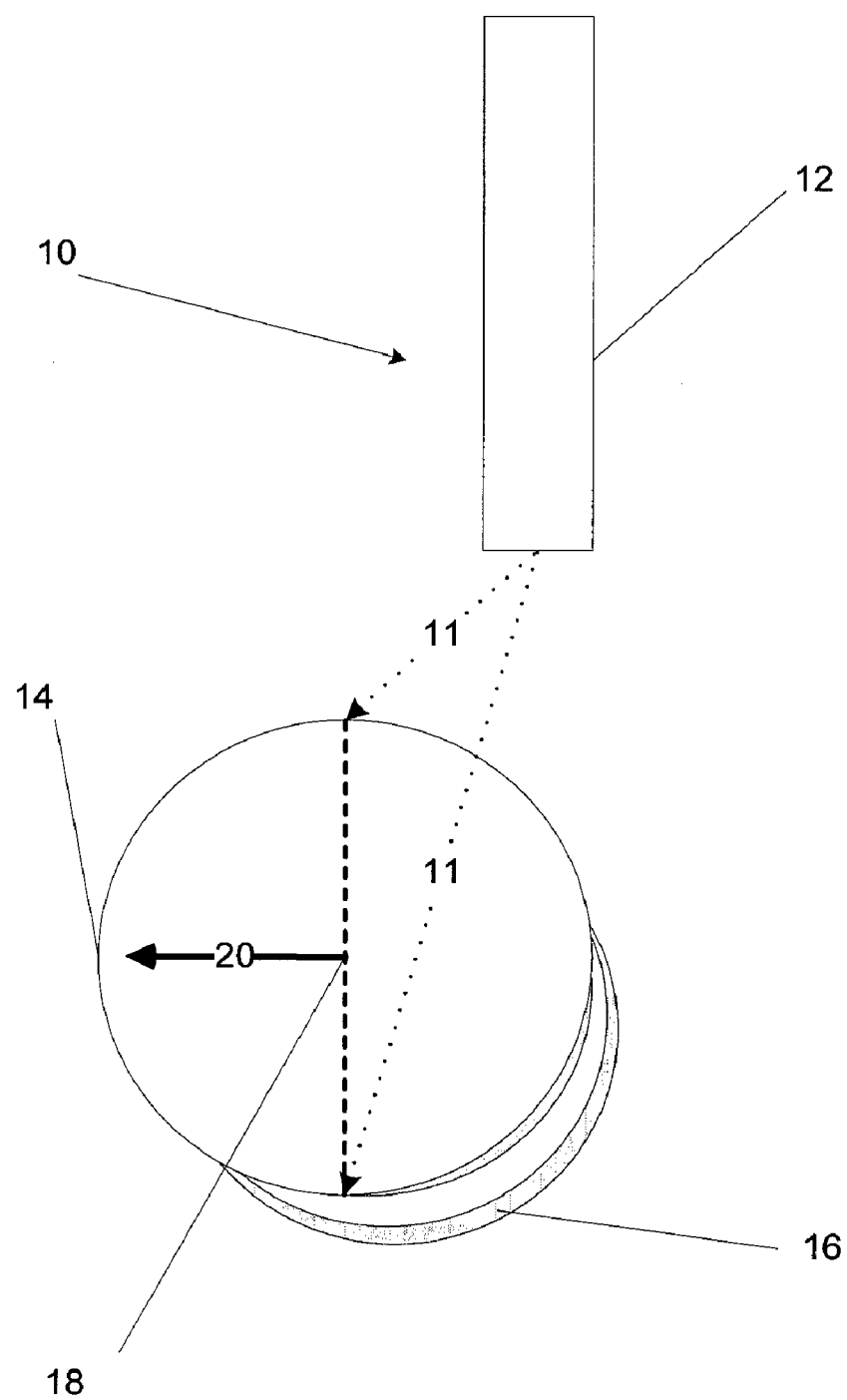
FIG. 1 is a schematic diagram showing one configuration of apparatus comprising a laser which includes focusing optics, SMA thin film, and substrate used in the method of the invention to make single crystal SMA thin film.

In its broadest concept, the present invention provides fabrication methods and articles of manufacture comprising a thin film component made of a single crystal SMA material which has the property of enabling a large repeatable strain recovery, and methods of making such devices. Single crystal SMA material has been described in PCT Publication WO 2005/108635 to TiNi Alloy Company for Single Crystal Shape Memory Alloy Devices and Methods.

Within the past two decades, SMA materials have become popular for use as actuators due to their ability to generate substantial stress during shape recovery of large strains during temperature-induced phase transformation. The energy density of such actuators is high compared to other alternatives, such as electromagnetic, electrostatic, bimetals, piezoelectric, and linear and volume thermal expansion effects of ordinary materials. The operating cycle of an SMA actuator includes deformation during or after cooling, and subsequent heating which results in a temperature-induced phase transformation and recovery of the deformation. SMA actuation is favored where relatively large force and small displacements are required in a device that is small in size and low in mass. Some processes have been developed for thin film memory alloy manufacturing. See, e.g., U.S. Pat. Nos. 6,790,298 to Johnson et al. for Method of Fabrication of Free Standing Shape Memory Alloy Thin Film; 5,061,914 to Busch et al. for Shape-Memory Alloy Micro-Actuator; 6,537,310 to Palmaz et al. for Endoluminal Implantable Devices and Methods of Making Same; and 6,605,111 to Bose et al. for Endovascular Thin Film Devices and Methods for Treating and Preventing Stroke; and U.S. Patent Publication 2004/0014253 to Gupta et al. for Three Dimensional Thin Film Devices and Methods of Fabrication.

Shape memory is the ability of certain alloys to recover plastic deformation, which is based on a diffusionless solid-solid lattice distortive structural phase transformation. Shape memory alloys have the ability to undergo mechanical twinning, or a martensitic or similar reversible solid-state transformation which involves a dimensional change, occurring usually over a narrow temperature change. Twinning structures typically appear at right angles to each other in thin film which can impact the dimensional change. The mechanical twinning process generally enables a shape produced in one state to be recorded if the temperature is altered back again despite the shape having changed in the interim. The performance of shape memory alloy based actuators strongly depends on the amount of recoverable deformation. In turn, recoverable deformation itself is a function of the lattice distortions which take place during martensitic phase transformation in the particular SMA. For an individual grain (single crystal) of SMA, the amount of possible recoverable strain after uniaxial loading depends on the particular crystallographic orientation of the deformation tensor relative to the crystallographic axes of the high temperature (austenite) phase and the sign of applied load (tension or compression). As described above, the crystal(s) can be described as textured because the thinness of the film results in an apparent loss of some of the crystal variants. For example, alignment of crystallographic axes. An advantage of the material produced according to this method is that the material advantages of single crystal bulk shape memory alloy (e.g., increased recoverable strain and constant stress) is extended to the thin film by growing the crystal in such a way that it has preferred crystallographic orientation, or texture.

For a given deformation mode, the recoverable strain is strongly orientation dependent, and for the various crystallographic directions it differs by approximately a factor of two. The recoverable deformation of polycrystalline SMA alloys, due to the lattice distortion during diffusionless solid-solid phase transition, is substantially lower than is theoretically possible for a given material. The main reason for this is that for a conglomerate of randomly oriented grains (as is normally the case for polycrystalline materials), the average deformation will always be less than the maximum available value for a given grain. The diffusionless nature of phase transitions in SMA results in strict lattice correspondence between the high temperature (austenite) and low temperature (martensite) lattices. As the symmetry of the martensite lattice is lower than that of austenite, maximum deformation in each grain can only be attained in one particular crystallographic direction. This means that for randomly oriented grains (as normally is the case for polycrystalline materials), the average deformation will be at least a factor of two less than the maximum potentially available deformation.

The restrictions imposed on a polycrystalline body by the deformation mechanism is another reason for diminished recoverable deformation in polycrystals as compared with a single crystal. To maintain integrity of the polycrystal, deformation each particular grain has to be less than that corresponding to the theoretical limit for lattice distortion. Therefore, for polycrystalline material, resultant recovery is the vector sum of particular grain deformations over the whole range of grain orientations, and is significantly smaller than the maximum value for an individual single crystalline grain.

By comparison, recoverable deformation close to the theoretical value (lattice distortion) can be achieved in single crystalline SMA. Thus single crystalline SMA is desirable for its ability to achieve recoverable deformation close to the theoretical value. In addition to the substantially increased recoverable deformation properties, absence of grain boundaries in the single crystalline SMA results in increased strength and longer fatigue life. Specifically, as a single crystal, the strength of the grain in CuAlNi SMA can be as high as 800 MPa with the potential limit for recoverable deformation up to 9 percent and even higher for special deformation modes. As will be appreciated by those skilled in the art, the strength of the grain for TiNi can be even higher. Additional advantages of a single crystal SMA include the ability to thermally induce phase transformation and contribute to the recoverable deformation, as in the case for polycrystals, as well as the ability for the thermally induced phase transformation to contribute to the stress-induced martensite-to-martensite phase transitions.

TiNi thin film is fabricated in a different set of processes than bulk material. Sputter deposition leaves the material in an amorphous state. This provides an opportunity for crystallization in a specific direction which can be achieved using the methods described herein (giving a preferred orientation) and as a single crystal.

The advantages of single crystal SMA over polycrystal SMA include:

1. Greater than 9% strain recovery. There is a three fold gain in performance over the conventional SMA materials made from bulk materials. Depending on how the sample is used, the greater than 9%, for example, can either be used in the high temperature state (when in austenite phase) as a hyperelastic spring, or deformed 9% (when in martensite phase) and then heated to recovery as an actuator. Thus, <100> is the preferred direction for an alloy of Cu—Al—Ni according to the crystallographic index and <111> is the preferred direction for an alloy of TiNi according to the crystallographic index. The mechanical properties are not isotropic in materials that undergo a stress-induced martensite transformation. As a result, a wire of single crystal Cu—Al—Ni can be elongated more than 9% and will recover its shape when the deforming force is removed. In contrast, perpendicular to the long axis of the wire it cannot be deformed more than about 4% without breaking.

2. True Constant Force Deflection. Unlike polycrystalline materials which reach their strain/stress plateau strength in a gradual fashion and maintain an upward slope when deformed further, single crystal SMA materials have a very sharp and clear plateau strain/stress that provides a truly flat spring rate when deformed up to 9%. As a result, these single crystal SMAs can be described as exhibiting hyperelastic properties because the range of strain recovery is far beyond the maximum strain recovery of both conventional polycrystalline SMA materials and non-SMA metals and allows. An additional benefit is that the strain recovery for materials exhibiting hyperelastic properties is repeatable. Thus, for example, single crystal SMAs exhibiting hyperelasticity benefit from a second stress plateau that can increase the total recoverable strain to 22%.

3. Very Narrow Loading-Unloading Hysterisis. As a result there is substantially the same constant force spring rate during both loading (increasing stress) and unloading (decreasing stress).

4. Recovery Which is Repeatable and Complete. A drawback of polycrystalline SMA materials is the settling that occurs as the material is cycled back and forth. The settling problem requires the polycrystalline SMA to be either trained as part of the manufacturing process or designed into the application for use such that the permanent deformation which occurs over the first several cycles does not adversely effect the function of the device. In contrast, single crystal SMA do not develop permanent deformaties.

5. Very Low Yield Strength when Martensitic. The ability to provide a low yield strength when in the martensitic phase is a property that is useful for designing devices that have two states, e.g. actuators which are two-way.

6. Ultra-Low Transition Temperature. Single crystal SMA made from Cu—Al—Ni can be manufactured with transition temperatures close to absolute zero (−270 Celsius). This compares to SMA materials made from TiNi which have a practical transition temperature limit of −100 Celsius. An advantage is the single crystal SMA use in various cryogenic applications as well as the ability to be used as a valve to control flow of cooling medium.

7. Intrinsic Hyperelastic Property. TiNi SMA can be conditioned, through a combination of alloying, heat treatment and cold working, to have superelastic properties. Single crystal Cu—Al—Ni SMA has intrinsic hyperelastic properties. Thus, a single crystal of Cu—Al—Ni is hyperelastic immediately after being formed (pulled and quenched) with no further processing required.

8. Increased Thermal Cycle Rate. An increased thermal cycle rate, up to at least a kilohertz can be observed. This provides improves strength and fatigue properties compared to bulk materials. Additionally the smaller crystal size typically has no inclusions which means that micro electro-mechanical systems (MEMS) fabrication techniques can be applied to mass production.

FIG. 1 schematically illustrates a system for carrying out the method of the invention. Apparatus 10 comprises a heat source 12. Heat source 12 can include, but is not limited to, lasers (which could also include suitable focusing optics), intense light sources capable of delivering light in the infrared or visible wavelengths, and scanning electron beams. A SMA film 14 layer is provided over a substrate 16 used in fabricating single crystal formation in a thin film. The crystals forming the thin film 14 may have an anisotropic behavior that is different in different crystal directions. For example, for a Cu—Al—Ni alloy, more than twice the recordable strain in a first plane (e.g. within a plane on an x-axis) may be observed than in planes perpendicular to the first plane. Crystals produced according to the methods of this invention are capable of forming films 1-2 microns thick. This thickness corresponds to a few crystal grains in diameter and provides a good candidate for oriented crystal growth. Further, films as thin as 70 nm having crystal sizes 1-2 microns in diameter can be produced. These films employ 2-dimensional crystals which are advantageous for growing oriented crystals.

Apparatus 10 is scanned in a beam 11 over the surface of film 14 which is carried on substrate 16. No special processing of the substrate is required to practice the invention. However, as will be appreciated by those skilled in the art, MEMS processes, such as the use of a sacrificial layer for subsequent removal of film from the substrate, is allowed. The substrate may be any suitable size. The beam forms a strip which is wide enough to make a swath or sweep, shown by dashed line 18. Arrow 20 shows, for example, the direction that the beam travels across the surface of the amorphous material during the method. The beam power as well as the beam energy absorption property of the film surface must be sufficient to enable heating of the SMA material to crystallization temperature very rapidly so that only a single crystal direction propagates. The energy required for crystallization of a particular alloy would be known to a person skilled in the art from a differential scanning calorimetry (DSC) measurement and could vary. The apparatus, such as a laser, scans the surface of the material at a speed that is sufficient to enable growth of a single crystal. Material behind the beam is cooled rapidly so that the crystal formed under the beam is stable, that is, no re-crystallization takes place.

In a specific embodiment, a laser with optics is used to produce a line focus. The line focused laser forms a light beam that sweeps, in a narrow band or swath, over the surface of the material.

Special processes may be needed to initiate crystal growth. It may require a seed to start and propagate in the right direction. It may be advantageous to start with a spot and fan it out so that a single crystal forms and grows outward as well as forward. This resembles the method used in pulling Si and Cu—Al—Ni crystals. As will be appreciated by those skilled in the art, success in growing a single crystal thin film from the amorphous state depends on several factors. Sufficient heat must be input to raise the temperature of the film to the crystallization temperature. As discussed above, the amount of heat required would be apparent from the DSC measurements.

As will be appreciated, heat of crystallization will contribute to the change in temperature, but not significantly. The heat of crystallization is typically 10-50 Joules per gram. The heat required to raise the temperature depends on the materials and on the temperature and is typically hundreds of Joules per gram. Heating is rapid so as to minimize the heat transferred to the substrate. Cooling is typically rapid (and can thought of as equivalent to quenching) because the substrate 16 is a large heat sink compared to the thin film 14.

The rate of travel of the heated line across the surface must closely match the speed at which crystals grow. Crystal growth speed depends on the sample thickness, so this rate must be adjusted to produce complete crystallization. Crystals typically grow in a period of seconds in very thin film. Optimization is possible and must be done experimentally. If the crystallization is incomplete, a subsequent heat treatment might be used fill in the places that are not completely crystallized. As will be appreciated by those skilled in the art, smaller volumes of crystals may be heated using an electron beam instead of a laser. Further, film thicknesses can range from, for example, 100 nanometers to 10 microns.

One embodiment of a method of the invention includes forming a crystalline thin film. The method comprises the steps of growing the film from an amorphous state by causing a narrow band of the film to be heated to the crystallization temperature, and moving the heated band across the expanse of film.

Another embodiment is the method of crystallizing an amorphous thin film comprising the step of moving a line-focused laser beam over the surface of the film. Yet another embodiment is the method that results in a single crystal thin film by the steps of growing the film from an amorphous state by causing a narrow band of the film to be heated to the crystallization temperature/and moving the heated band across the expanse of film. Still another embodiment is an article of thin film formed by crystallization of an amorphous thin film fabricated by the steps of growing the film from an amorphous state by causing a narrow band of the film to be heated to the crystallization temperature, and moving the heated band across the expanse of film. Another embodiment is an expanse of thin film of titanium-nickel that is comprised of a single crystal.

Figure 2:
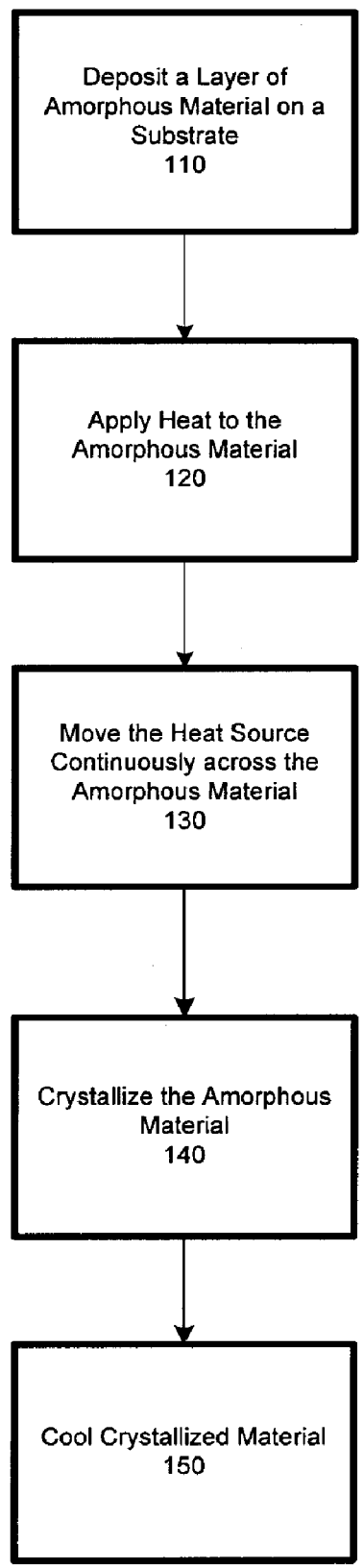
FIG. 2 illustrates method steps of manufacturing a single crystal thin film.

FIG. 2 illustrates a set of method steps of manufacturing a single crystal thin film. In an embodiment, the method includes depositing a layer of amorphous material on a substrate 110. Thereafter heat is applied to the amorphous material 120. The heat is applied, for example, by a laser, light source, or other mechanism capable of achieving the desired temperature. The heat is applied in a narrow strip or band, for example, in a sweeping motion across the surface of the amorphous material in a direction (20 in FIG. 1). One or more passes of the heat strip can be applied until the desired result is achieved. The one or more passes are typically in the same direction in order to promote selective crystal growth in a single direction. Thus, for example, the heat source can be turned on, applied to the surface of the substrate by sweeping across the surface of the substrate in a single direction, turned off (or directed away from the surface) and returned to the start position, and then applied to the surface again in the same direction. This process is repeated as often as required to achieve the desired results. The heat source is moved continuously 130 across the amorphous material to heat sequential strips of material; crystallization of the amorphous material 140 occurs. Thereafter a the crystallized material is cooled 150. The cooling step occurs quickly and can be achieve by providing, for example, a heat sink. Additionally, the method can be performed such that a preferred crystal orientation is imparted to the thin film expanse. The method can include the use of a seed crystal to initiate the crystallization process, if desired. Additionally, the amorphous expanse can be crystallized into material that is superelastic at room temperature.

Figure 3A:
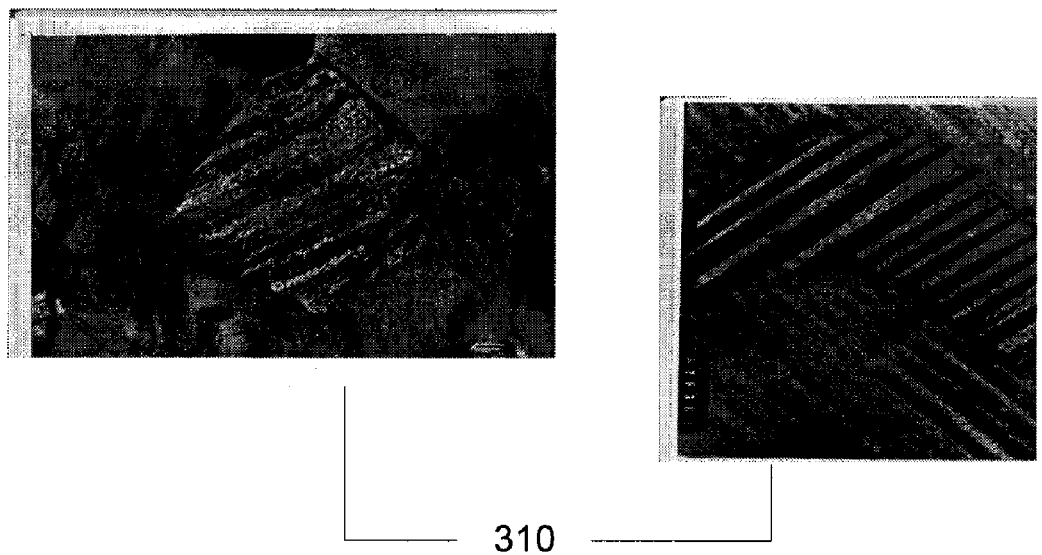
FIGS. 3A-B are scanning and transmission electron micrographs illustrating a crystal formed from depositing an amorphous layer onto a substrate and crystallizing the layer with heat treatment.
Figure 3B:
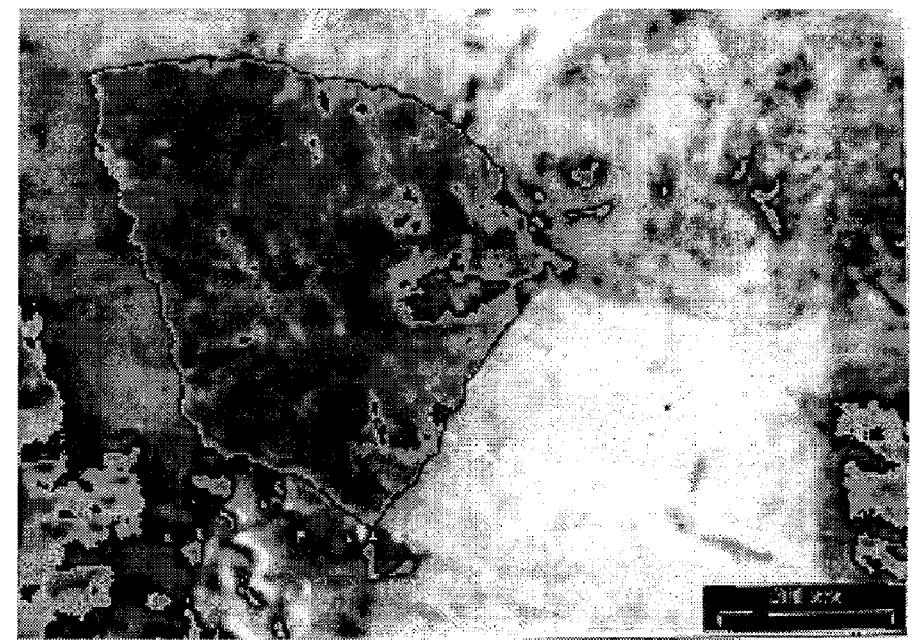

FIG. 3A are scanning electron microscope (SEM) images 310 of a shape memory thin film formed by vacuum sputter deposition and heat crystallization. The grain size is about 1-3 micrometers in size. Twinning is observed, generally consisting of plates of sub-micrometer size needles lying at right angles to each other. FIG. 3B is a transmission electron micrograph (TEM) image 320 of a single grain of sputter-deposited shape memory alloy about 70 nanometers thick. The grain is about 1 micrometer in diameter, which is more than ten times its thickness.

As mentioned above, the single crystal superelastic metal alloy thin film can be used to create a wide variety of devices, as would be appreciated by those skilled in the art. For example, among the three-dimensional thin film shapes and their possible use for medical applications are the following: cone shapes adapted for use to retrieve blood clots, particularly clots causing ischemic stroke; cylindrical shapes adapted for use as stents to support blood vessels from collapse and stenosis, and to permit treatment of intracranial aneurysms; cylindrical shapes adapted for use as a scaffold structure for making artificially grown blood vessels of all sizes; hemispherical shapes adapted for insertion into aneurysms to isolate the aneurysm from blood flow in parent blood vessels; dome-shaped structures having multiple layers of thin film are intended to be used in intraocular devices for lens implantation.

Cones or cylinders which are formed from more than two layers of thin film can be adapted to create channels (or pockets) between the two layers allow the insertion of an outer structure into the thin film structure. In the context of blood clot retrieval devices, a set of such pockets are used as means for attaching wires or other external parts of a catheter to the thin film cone and cylinders.

Multiple-part devices of the type described are used for blood vessels. A short segment of a cylindrical shaped device can be inserted into each end of a pair of blood vessels to be joined, in such a way that they exert an outward pressure on the blood vessel lumen tending to keep it open and to return it to an open shape when crushed. A third cylinder, having a larger diameter, is then placed over the ends. This member will exert an inward pressure. The result is an anastomosis of the two blood vessel ends, in which the blood vessel wall is gently pressed between the two inner cylinders and the outer cylinder. The outer cylinder will be stretched so that when it is placed it gently forces the two ends of the blood vessel against each other to form a seal and to promote healing.

Deploying or implanting medical devices using microcatheters through tortuous small blood vessels, in the brain for example, requires devices that are extremely flexible and miniaturized. Such flexible and miniaturized devices are made by the thin film deposition methods of the invention creating extremely thin films with thickness less than 50 mm. Although thin film can be fabricated using several deposition techniques, sputter deposition techniques are mainly used for fabricating thin film stents.

Figure 4A:
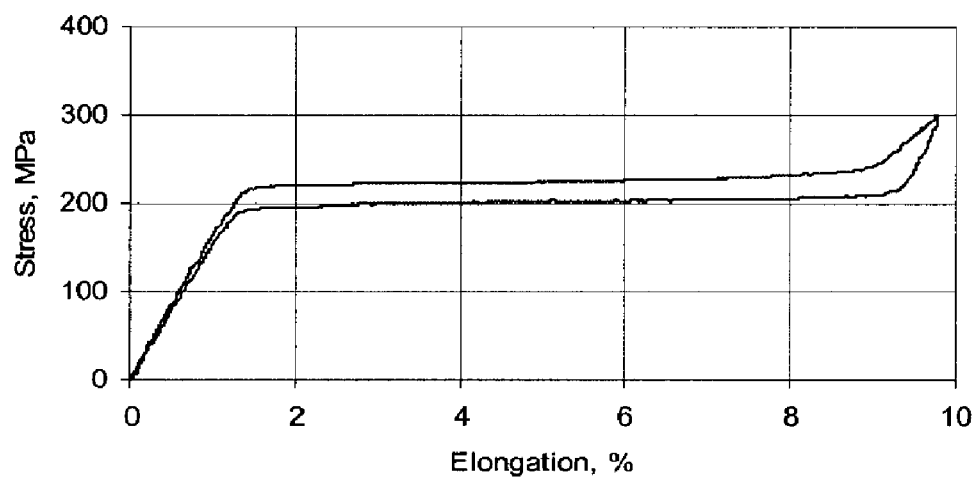
FIG. 4A is a graph showing single crystal SMA stress-strain property.
Figure 4B:
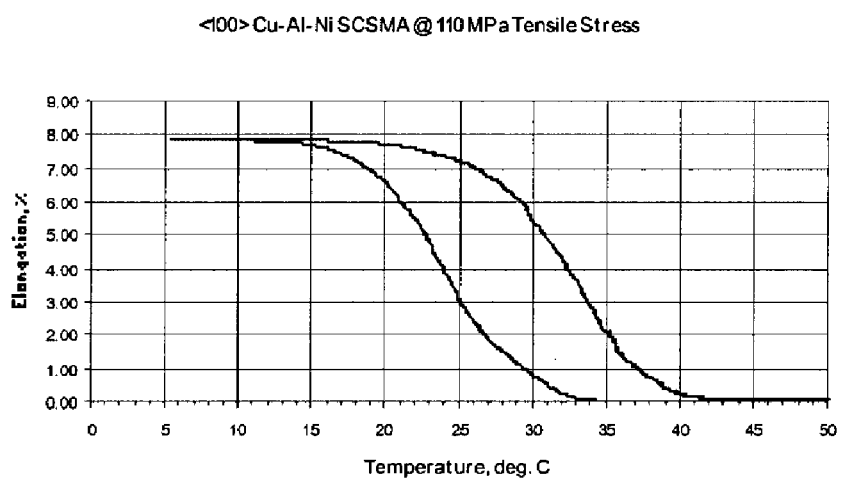
FIG. 4B is a graph showing the single crystal SMA shape memory property.

As illustrated in FIG. 4A, the stress-strain property of single crystal SMA is 100% superelastic, recovering up to 9% strain (<100> direction) when in the austenitic state. The plateau stress depends on the transition temperature and increases at a rate of 3.5 MPa/° C. a graph showing single crystal SMA stress-strain property. As would be appreciated by those skilled in the art, the transition temperature is dependent upon the composition and can be tuned to between −270° C.−+150° C. Thus, plotting force versus elongatation (stress v. strain), for an ordinary wire produces a straight line. The stress-strain curve for a superelastic wire has a plateau because elongation takes place at nearly constant force. This feature makes single crystal SMA an alternative for stents and springs. Springs of this material can store 20-30 times as much mechanical energy as the same spring made of steel. FIG. 4B is a graph showing the single crystal SMA shape memory property. As shown in FIG. 4B, the thermally induced transition from martensite to austenite can be used as an actuator. The material while in a low temperature state (martensite) can be deformed up to 8% and then heated to full recovery by heating it above its transition temperature, which largely depends on the composition. This process of deformation and heating can result in powerful actuators capable of delivering recovery forces (stresses) up to 500 mPa.

As will be appreciated by those skilled in the art, in addition to making single crystal SMA, as described above, this method can be used to make thin film SMA consisting of multiple crystals that have the same crystalline orientation that lie parallel to each other. Such an arrangement would have the benefit of enhanced strain recovery, such as that exhibited by the single crystal SMA. In order to achieve the multiple crystal embodiment, the method could be adapted to include, for example, crystallizing a first layer of amorphous material (as described above), depositing another thin layer of amorphous material and then applying the crystallization process to that layer (and repeating as desired). Alternatively, a first crystal may be formed and then one or more subsequent crystals formed using the techniques described herein. Other adaptations of the methods and process would be apparent to those skilled in the art upon reviewing this disclosure.

A variety of other devices, components of devices and improved devices can be made using the materials described herein. For example, microactuators, miniature valves, electric switches, relays, optical switches, a variety of medical devices, improves stents, stent covers, anastomosis devices, self-expanding stents or stent covers, to name a few. See, for example, the disclosures of U.S. Pat. No. 5,325,880 to Johnson et al. for Shape-Memory Alloy Film Actuated Microvalve; U.S. Pat. No. 5,903,099 to Johnson et al. for Fabrication System, Method and Apparatus for Microelectromechanical Devices; U.S. Pat. No. 5,960,812 to Johnson for Fluid Flow Control Valve; U.S. Pat. No. 6,470,108 to Johnson for Optical Switching Device and Method; U.S. Pat. No. 6,533,905 to Johnson et al. for Method for Sputtering TiNi Shape-Memory Alloys; U.S. Pat. No. 6,614,570 to Johnson et al. for Shutter for Fiber Optic Systems; U.S. Pat. No. 6,642,730 to Johnson et al. for Thin Film Shape Memory Alloy Actuated Microrelay; U.S. Pat. No. 6,669,795 to Johnson et al. for Methods of Fabricating High Transition Temperature SMA, and SMA Materials Made by the Methods; U.S. Pat. No. 6,729,599 to Johnson for Liquid Microvalve; U.S. Pat. No. 6,742,761 to Johnson et al. for Miniature Latching Valve; U.S. Pat. No. 6,746,890 to Gupta et al. for Three Dimensional Thin Film Devices and Methods of Fabrication; and U.S. Patent Publications 2003/0170130 to Johnson for Micro-Dosing Pumps and Valves; 2003/0002994 to Johnson et al. for Thin Film Shape Memory Alloy Actuated Flow Controller;

2002/0195579 to Johnson for Liquid Microvalve; 2001/0039449 to Johnson et al. for Thin-Film Shape Memory Alloy Device and Method; and 2002/0071167 to Johnson et al. for Shutter for Fiber Optic Systems.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for making a single crystal shape memory alloy thin film comprising the steps of:
    depositing a thin film layer of amorphous shape memory alloy material on a substrate;
    applying a strip of heat to the amorphous shape memory alloy material to form a crystallization front along the strip;
    moving the strip of heat across the amorphous shape memory alloy material in a direction to move the crystallization front across the material;
    crystallizing the amorphous material into crystallized material having a single crystal crystallographic orientation; and
    cooling the crystallized material with a heat sink.

2. The method of claim 1 wherein the crystallization step comprises using a seed crystal to initiate the crystallization process.

3. The method of claim 1 wherein the crystallized material is superelastic at room temperature.

4. The method of claim 1 wherein the shape memory alloy material is initially a polycrystalline shape memory alloy.

5. The method of claim 1 in which the heat is provided by a device selected from the group consisting of: laser, infrared wavelength light source, visible wavelength light source.

6. The method of claim 1 in which the heat is provided by a scanning electron beam.

7. A method for forming a thin film, single crystal shape metal alloy comprising the steps of:
    sputter depositing a thin film of amorphous shape memory alloy material onto a substrate;
    heating the thin film amorphous shape memory alloy material with a narrow band of heat so that it reaches its crystallization temperature in the narrow band;
    moving the narrow band of heat across the thin film to create a moving crystallization front having a single crystal crystallographic orientation; and
    cooling behind the crystallization front to stabilize the single crystal crystallographic orientation formed.

8. The method of claim 7 further comprising using a seed crystal as a starting material.

9. The method of claim 7 wherein the crystallized material is superelastic at room temperature.

10. The method of claim 7 wherein the shape memory alloy material is initially a polycrystalline shape memory alloy.

11. A method of manufacturing a device having a thin film of single crystal shape memory alloy comprising the steps of:
    depositing a layer of amorphous shape memory alloy material on a substrate;
    applying a strip of heat to a portion of the amorphous material to form a crystallization front along the strip;
    moving the strip of heat across the amorphous shape memory alloy material to move the crystallization front across the material;
    crystallizing the amorphous shape memory alloy material into a single crystal crystallographic orientation;
    cooling the material behind the crystallization front with a heat sink; and
    manufacturing a device from the crystallized material.

12. The method according to claim 11 wherein the device is selected from the group consisting of: microactuator, valve, electric switch, relay, optical switch, stent, stent covers, and anastomosis devices.

13. The method of claim 12 wherein the shape memory alloy material is initially a polycrystalline shape memory alloy.

* * * * *